US008879056B2

(12) United States Patent
Zhao et al.

(10) Patent No.: US 8,879,056 B2
(45) Date of Patent: Nov. 4, 2014

(54) MULTI-SPOT ILLUMINATION FOR WAFER INSPECTION

(71) Applicant: KLA-Tencor Corporation, Milpitas, CA (US)

(72) Inventors: Guoheng Zhao, Milpitas, CA (US); Azmi Kadkly, Santa Clara, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 13/898,470

(22) Filed: May 21, 2013

(65) Prior Publication Data
US 2013/0250582 A1 Sep. 26, 2013

Related U.S. Application Data

(62) Division of application No. 13/187,375, filed on Jul. 20, 2011, now Pat. No. 8,462,329.

(60) Provisional application No. 61/369,638, filed on Jul. 30, 2010.

(51) Int. Cl.
G01N 21/00 (2006.01)
G01N 21/95 (2006.01)
F21V 5/00 (2006.01)

(52) U.S. Cl.
CPC ............ F21V 5/008 (2013.01); G01N 21/9505 (2013.01)
USPC .................... 356/237.2; 356/237.1

(58) Field of Classification Search
USPC .............. 356/239.7–239.8, 237.1–237.6; 359/566, 558, 563, 568, 572, 570, 565, 359/573, 742, 569, 209; 347/244, 241
See application file for complete search history.

(56) References Cited

U.S. PATENT DOCUMENTS

| 4,581,617 | A  | * | 4/1986  | Yoshimoto et al. | 347/239 |
| 6,473,233 | B1 | * | 10/2002 | Iizuka           | 359/566 |
| 6,795,199 | B2 | * | 9/2004  | Suhami           | 356/601 |
| 7,223,232 | B2 | * | 5/2007  | Mizuno           | 600/160 |

OTHER PUBLICATIONS

S. Self, "Focusing of spherical Gaussian beams", App. Opt., vol. 22, No. 5, P658, 1983.

* cited by examiner

Primary Examiner — Tri T Ton
(74) Attorney, Agent, or Firm — Ann Marie Mewherter

(57) ABSTRACT

Illumination subsystems for multi-spot wafer inspection are provided. One illumination subsystem includes a diffractive optical element configured to separate an illumination light beam into multiple light beams and a refractive lens array positioned in the path of the multiple light beams. The refractive lens array is configured to relay the laser beam waist at the diffractive optical element onto a wafer surface and to separately and simultaneously focus each of the multiple light beams to a wafer for inspection.

7 Claims, 9 Drawing Sheets

| Patch No. | Period (μ) | Groove Angle (°) |
|---|---|---|
| 0 | N/A | N/A |
| 1 & -1 | 63.503 | 0.00838 |
| 2 & -2 | 31.752 | 0.01676 |
| 3 & -3 | 21.168 | 0.02514 |
| 4 & -4 | 15.876 | 0.03351 |
| 5 & -5 | 12.701 | 0.04187 |

MULTI-SPOT ILLUMINATION FOR WAFER INSPECTION

BACKGROUND OF THE INVENTION

1. Field of the Invention

This invention generally relates to multi-spot illumination for wafer inspection. Certain embodiments relate to illumination subsystems configured to provide multi-spot illumination for wafer inspection using light having a relatively large bandwidth.

2. Description of the Related Art

The following description and examples are not admitted to be prior art by virtue of their inclusion in this section.

Inspection processes are used at various steps during a semiconductor manufacturing process to detect defects on wafers to promote higher yield and thus higher profits. To increase defect detection sensitivity, some inspection systems are designed to reduce surface scattering by reducing the size of the illumination spot on the wafer and compensating for the reduced size of the spot by illuminating multiple spots on the wafer simultaneously.

In some inspection systems, a diffractive optical element (DOE) is used to split a single laser beam into multiple laser beams, and an objective lens focuses the beams to form multiple spots. Typically, the DOE is placed at the back focal plane of the objective lens, while the focused spots are formed at the front focal plane of the objective lens. For example, as shown in FIG. 1, illumination light beam 10 may be directed to DOE 12. DOE 12 separates the illumination light beam into multiple light beams 14. The multiple light beams may be directed to objective lens 16 that is configured to focus the multiple light beams to focal plane 18 as individual, spatially separated spots on the focal plane. The focal plane may be the wafer plane.

The method shown in FIG. 1 works well when the laser bandwidth is relatively small. For relatively large bandwidth lasers such as relatively high power, solid state deep ultraviolet (DUV) lasers, the laser bandwidth is large enough to cause significant blur of the focused spots because of the angular dependence on wavelength by DOE diffraction. Therefore, illumination subsystems that use DOEs are currently limited to using relatively small bandwidth lasers.

Accordingly, it would be advantageous to develop a method of splitting a light beam, which has a relatively large wavelength bandwidth, into multiple light beams to generate diffraction-limited spots for wafer inspection.

SUMMARY OF THE INVENTION

The following description of various embodiments is not to be construed in any way as limiting the subject matter of the appended claims.

One embodiment relates to an illumination subsystem configured to provide illumination for wafer inspection. The illumination subsystem includes a diffractive optical element (DOE) configured to separate an illumination light beam into multiple light beams. The illumination subsystem also includes a compensating DOE positioned in the path of the multiple light beams. The compensating DOE has the same diffraction angle as the DOE but reverse in diffraction order. The illumination subsystem also includes one or more refractive optical elements positioned in the path of the multiple light beams exiting the compensating DOE and configured to separately and simultaneously focus each of the multiple light beams to a wafer for inspection. The illumination subsystem described above may be further configured as described herein.

Another embodiment relates to an illumination subsystem configured to provide illumination for wafer inspection. The illumination subsystem includes a DOE configured to separate an illumination light beam into multiple light beams. The illumination subsystem also includes a refractive lens array positioned in the path of the multiple light beams. Diameters of the multiple light beams at the back focal plane of the refractive lens array are $$W_2 = \frac{4\lambda f_1}{\pi W_0},$$

where $\lambda$ is the wavelength of the illumination light beam, $f_1$ is the focal length of a refractive lens positioned between the DOE and the refractive lens array, and $W_0$ is the diameter of the illumination light beam at the DOE. Diameters of the multiple light to beams at the focal plane of the refractive lens array are $$W_4 = \frac{4\lambda f_2}{\pi W_2} = \frac{f_2}{f_1} W_0,$$

where $f_2$ is the focal length of the refractive lens array. Diameters of the multiple hg beams at the refractive lens array are $$W_3 = W_0 \sqrt{\left(\frac{f_2}{f_1}\right)^2 + \left(\frac{4\lambda f_1}{\pi W_0^2}\right)^2}.$$

The refractive lens array is configured to relay the laser beam waist at the DOE onto a wafer surface and to separately and simultaneously focus each of the multiple light beams to a wafer for inspection. The illumination subsystem may be further configured as described herein.

In one embodiment, the compensating DOE is a one-dimensional chirped grating, and the one or more refractive optical elements include a cylindrical lens.

An additional embodiment relates to an illumination subsystem configured to provide illumination for wafer inspection. The illumination subsystem includes a set of beam splitters configured to separate an illumination light beam into multiple light beams and to separately and simultaneously direct the multiple light beams to multiple spatially separated spots on a focal plane. The illumination subsystem also includes one or more refractive optical elements configured to separately and simultaneously focus each of the multiple light beams from the focal plane to a wafer for inspection. The illumination subsystem may be further configured as described herein.

BRIEF DESCRIPTION OF THE DRAWINGS

Other objects and advantages of the invention will become apparent upon reading the following detailed description and upon reference to the accompanying drawings in which.

Figure 1:
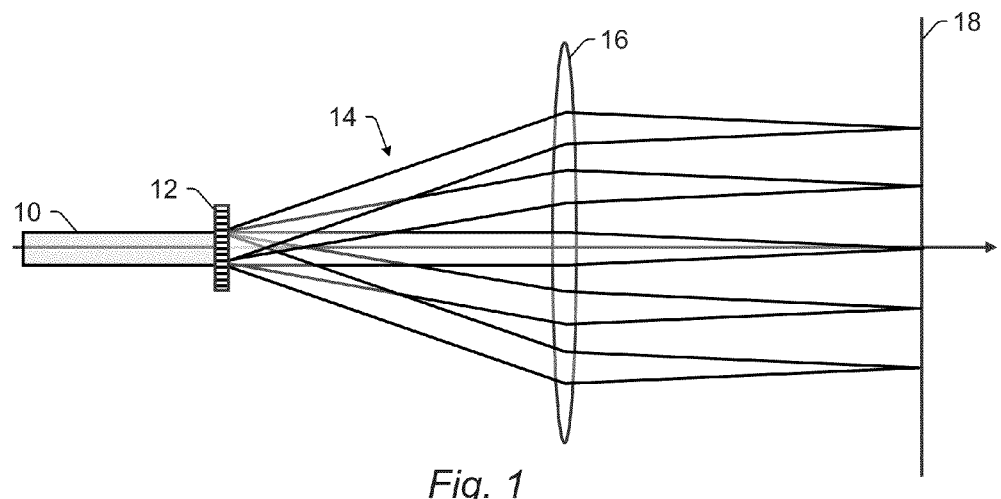
FIG. 1 is a schematic diagram illustrating a side view of one currently used illumination subsystem.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, each of the elements described herein may be any suitable commercially available elements that can be configured and used as described herein.

The embodiments described herein relate to illumination subsystems configured to provide illumination for wafer inspection. The wafer inspection may include any wafer inspection known in the art such as bright field (BF) wafer inspection, dark field (DF) wafer inspection, or BF and DF wafer inspection. In general, some embodiments described herein relate to illumination subsystems configured for compensating dispersion of a diffractive optical element (DOE) beam splitter to generate diffraction-limited spots. By compensating for the dispersion of a DOE beam splitter, the embodiments described herein advantageously enable the use of relatively high power ultraviolet (UV) lasers for multi-spot illumination.

One embodiment of the illumination subsystem includes a DOE configured to separate an illumination light beam into multiple light beams. In one embodiment, the illumination light beam is provided by a pulsed laser and has a central wavelength of 266 nm. In another embodiment, the bandwidth of the illumination light beam is equal to or greater than 10 pm. For example, for CW lasers at 266 nm, the laser bandwidth is typically much less than 1 pm. Therefore, for such lasers, the spot blur caused by the laser bandwidth is negligible. However, relatively high power deep ultraviolet (DUV) lasers may need to be used for high throughput wafer inspection tools, which are commercially available from KLA-Tencor, Milpitas, Calif. At the moment, relatively high power (e.g., 1 W to 5 W) 266 nm laser are pulsed lasers, which can have a relatively large bandwidth of up to a few hundred picometers. For example, for pulsed UV lasers, the laser bandwidth can be from a few tens of pm to a few hundreds of pm. Therefore, it is extremely difficult to generate substantially small spots with such large laser bandwidths using conventional DOE beam splitters, especially for a relatively large number of spots. The embodiments described herein, however, provide solutions for multi-spot illumination that enable the use of higher power, relatively large bandwidth DUV lasers.

Figure 2:
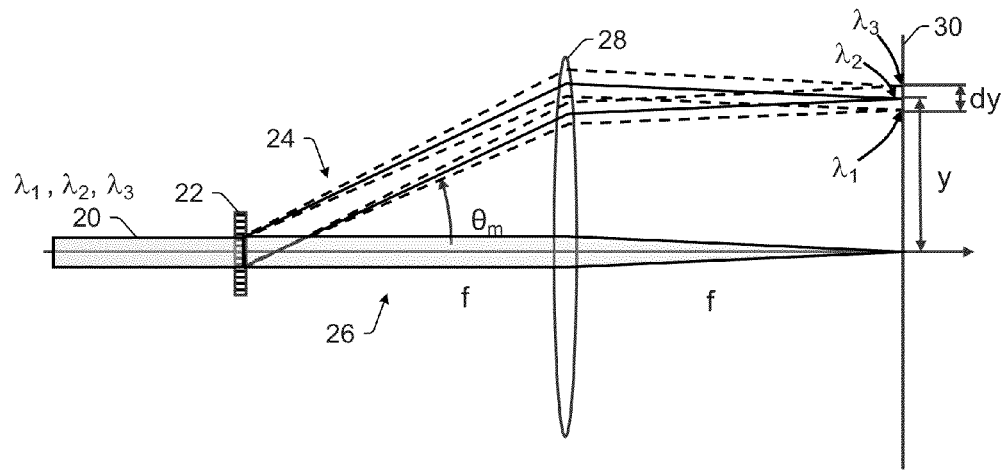
FIG. 2 is a schematic diagram illustrating the calculation of dispersion of a diffractive optical element (DOE)

The calculation of dispersion of a DOE is shown in FIG. 2. In particular, as shown in FIG. 2, illumination light beam 20 having a minimum wavelength $\lambda_1$, a central wavelength $\lambda_2$, and a maximum $\lambda_3$ may be directed to DOE 22, which is configured to separate the illumination light beam into multiple diffracted light beams. Only the $m^{th}$ order light beam 24 and the 0th order light beam 26 are shown in FIG. 2. The $m^{th}$ order diffracted light beams and the 0th order light beam may be directed to objective lens 28, which is configured to focus the light beams to focal plane 30, which may be a wafer plane. A DOE typically has a periodic wavefront modulation profile designed to generate multiple diffraction orders with equal efficiency. As shown in FIG. 2, the angular deviation of the $m^{th}$ order light beams is $\theta_m$. The angular deviation of the $m^{th}$ order is given by:

$$P \sin \theta_m = m\lambda \quad (1)$$

where P is the pitch of the grating profile, m is the number of the order, and $\lambda$ is the wavelength. For a focusing objective with focal length f, as shown in FIG. 2, the spot position y, as shown in FIG. 2, is given by:

$$y = f \sin \theta_m \quad (2)$$

For a laser with a bandwidth of $\delta\lambda$, which is typically much less than the central wavelength, that is, $\delta\lambda = \lambda_3 - \lambda_1 \Box \lambda_2$ we have:

$$\frac{dy}{y} = \frac{\delta\lambda}{\lambda} \quad (3)$$

where dy, as shown in FIG. 2, represents the spot blur in the y direction, at a field height of y. The spot blur is linearly proportional to the field height and the laser bandwidth. Table 1 lists the spot blur in urn for various field heights in mm and laser bandwidths in pm.

TABLE 1

| | Laser Bandwidth at 266 nm (pm) | | |
|---|---|---|---|
| Field (mm) | 50 | 100 | 150 |
| 0.25 | 0.05 | 0.09 | 0.14 |
| 0.5 | 0.09 | 0.19 | 0.28 |
| 0.75 | 0.14 | 0.28 | 0.42 |
| 1 | 0.19 | 0.38 | 0.56 |
| 1.25 | 0.23 | 0.47 | 0.70 |

As shown in Table 1, the spot blur is significant for a spot size of 1 um to 2 um.

As described above, for future wafer inspection tools, a higher power laser that has a larger wavelength bandwidth than currently used lasers may need to be used to meet higher sensitivity requirements. In addition, a relatively large field may be used to accommodate relatively large numbers of spots that may be used to meet throughput requirements. As shown in equation 3, spot blur caused by DOE dispersion increases linearly with laser bandwidth $\delta\lambda$ and field size y, and becomes a problem for small spot sizes down to 1 um to 2 um.

Another effect of the DOE dispersion, also demonstrated in Table 1, is the variation of spot size versus field. This results in a non-uniform response of defect sensitivity across the field. Therefore, there is a need for correcting the dispersion of the DOE and eliminating spot blur.

Figure 3:
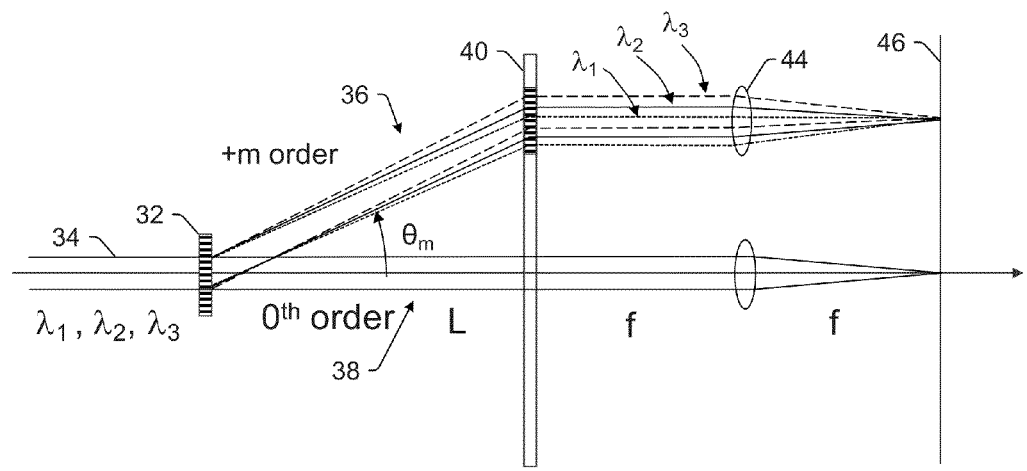
FIGS. 3-7 are schematic diagrams illustrating side views of embodiments of illumination subsystems.

One embodiment of the illumination subsystem is shown in FIG. 3. The illumination subsystem includes DOE 32 configured to separate illumination light beam 34 into multiple light beams 36 and 38. As shown in FIG. 3, the illumination light beam has wavelengths $\lambda_1$, $\lambda_2$, and $\lambda_3$. Multiple light beams 36 are the +1 order diffracted light beams. The DOE may also be configured to allow 0th order light beam 38 to pass through the DOE. The multiple light beams may also include other light beams having other orders that are not shown in FIG. 3 for the sake of simplicity.

The illumination subsystem also includes compensating DOE 40 positioned in the path of the multiple light beams. The compensating DOE has the same diffraction angle as the DOE but reverse in diffraction order. For example, the dispersion of a diffraction grating can be compensated by another grating that has the same diffraction angle but reverse in diffraction order. The diffraction angle $\theta_m$ of the $m^{th}$ order of a DOE with a pitch of $P_0$ is given by:

$$P_0 \sin \theta_m = m\lambda \quad (4)$$

The diffraction angle $\theta_n$ of the $m^{th}$ order exiting the compensating DOE is given by:

$$P_m(\sin \theta_n - \sin \theta_m) = n\lambda \quad (5)$$

where $P_m$ is the grating pitch of the $m^{th}$ compensating grating. In order for all rays at different wavelengths to arrive at the same focal point, they need to be parallel after exiting the compensating DOE, that is, $\theta_n = 0$ for all wavelengths:

$$P_m(-\sin \theta_m) = n\lambda \quad (6)$$

Therefore, $$P_m = -P_0 \frac{n}{m} \quad (7)$$

In one embodiment, the compensating DOE diffracts only one diffraction order of each of the multiple light beams. For example, in one embodiment, the compensating DOE diffracts only the −1 order of each of the multiple light beams, as shown in FIG. 3. For example, one solution is to have a compensating DOE only diffracting the −1 order. Therefore, the pitch of the compensating DOE is given by:

$$n = -1 \quad (8)$$
$$P_2 = \frac{P_1}{m}$$

In one embodiment, the compensating DOE is a transmission grating that satisfies the Bragg condition. In another embodiment, the compensating DOE is a blazed transmission grating. For example, a grating that only diffracts the −1 order is fundamentally a relatively thick transmission grating that satisfies the Bragg condition or a blazed transmission grating which can be manufactured with modern lithography methods and systems. However, the order that is only diffracted by the compensating DOE is not necessarily the −1 order. For example, for the −m order the diffraction order of the compensating DOE would be +1. In other words, the compensating DOE may diffract only one reversed diffraction order.

Figure 4:
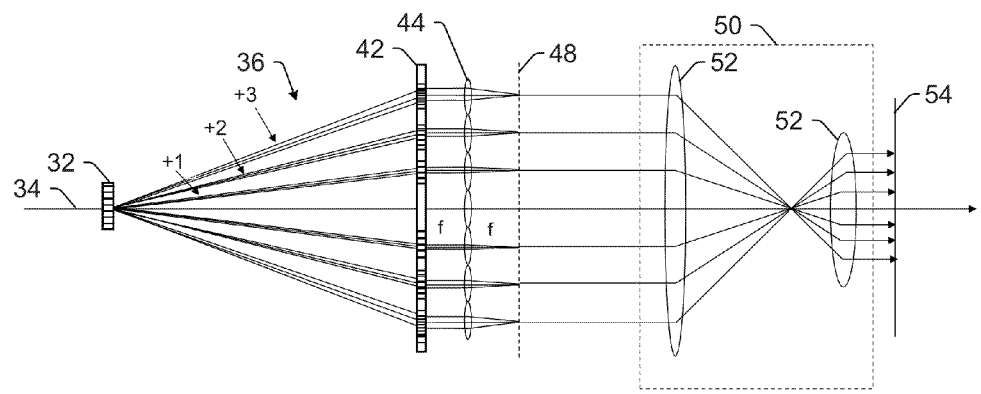

In an embodiment, the compensating DOE includes multiple gratings having different pitches. In this manner, the beam splitting DOE (or grating) generates multiple is beams with different angles, and the compensating DOE (or grating) may have multiple gratings, each one reverses the corresponding beam from the beam splitting DOE. For example, as shown in FIG. 4, DOE 32 diffracts light beams for each of the +1 order, the +2 order, the +3 order, etc. Compensating DOE 42 includes multiple gratings having different pitches. The different pitches may correspond to the different orders, respectively. For example, the grating pitch for the +1 order may be $P_0$, the grating pitch for the +2 order may be $2P_0$, the grating pitch for the +3 order may be $3P_0$ and so on. The grating pitch for compensating the dispersion of the $m^{th}$ order has a pitch of $1/m$ of the periodicity of the DOE.

The illumination subsystem also includes one or more refractive optical elements positioned in the path of the multiple light beams exiting the compensating DOE and configured to separately and simultaneously focus each of the multiple light beams to a wafer for inspection. In one embodiment, the one or more refractive optical elements include lens array 44 shown in FIGS. 3 and 4 that is configured to separately and simultaneously focus each of the multiple light beams to the wafer. For example, an individual lens of the lens array focuses one of the light beams separately from the light beams focused by the other lenses of the array. As shown in FIGS. 3 and 4, lens array 44 may have a focal length of f. In the configuration shown in FIG. 3, focal plane 46 may be the wafer plane. In the configuration shown in FIG. 4, focal plane 48 may be an intermediate local plane of the illumination subsystem, which may be the back focal plane of other refractive optical elements described further herein. In some instances, a field stop (not shown) may be positioned at focal plane 48.

In one embodiment, the multiple light beams are spatially separated from each other at the compensating DOE and at the one or more refractive optical elements. For example, the multiple light beams preferably are substantially separated when they arrive at the compensating DOE and preferably remain separated at the lens array. The distance between the lenses is determined by the spot separation, which limits the working distance achievable with the lens array.

In one embodiment, the one or more refractive optical elements include a lens array, which may be configured as described herein, to separately and simultaneously focus each of the multiple light beams and relay optics configured to separately and simultaneously relay the focused multiple light beams from the lens array to the wafer. For example, as shown in FIG. 4, the one or more refractive optical elements may include relay optics 50, which may include refractive lenses 52. Relay optics 50 are configured to relay the multiple light beams from focal plane 48 to focal plane 54, which may the sample surface or wafer plane. Relay optics may be used when a relatively long working distance is required. When relay optics are used, the spot size at the focal plane of the lens array is fairly flexible. Preferably, the relay optics have a demagnification since the lens array typically has a lower numerical aperture (NA) and the separation between the lenses of the lens array needs to be relatively large. The relay optics may include any suitable refractive optical elements such as a tube lens, a relay lens, a collimating lens, a focusing lens, a condenser lens, or some combination thereof.

Figure 5:
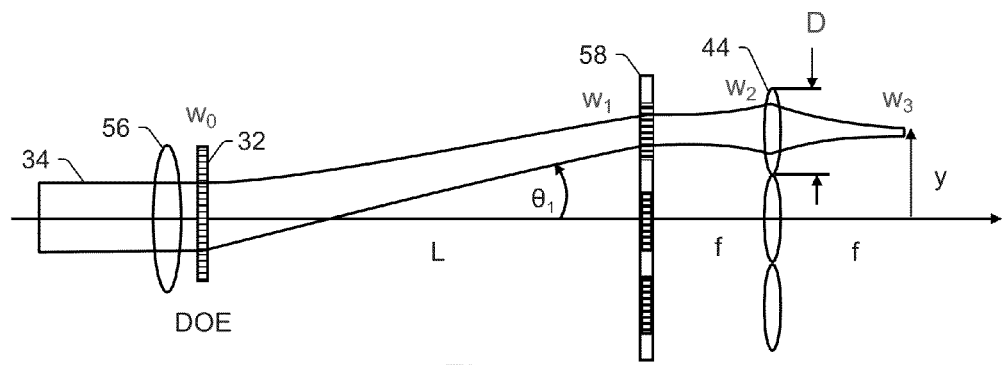

The illumination subsystem may also include one or more other refractive optical elements configured to direct the illumination light beam to the DOE. For example, as shown in FIG. 5, the illumination subsystem may include refractive lens 56 configured to direct illumination light beam 34 to DOE 32. The Gaussian beam waist, $W_0$, is located at the DOE. This embodiment of the illumination subsystem also includes compensating DOE 58, which in this embodiment is an array of local gratings with corresponding grating pitches. Light exiting the compensating DOE may be directed to one or more refractive optical elements, which in this embodiment includes lens array 44. In a preferred embodiment as shown in FIG. 5, if the first Gaussian beam waist, $W_1$, is located at compensating DOE 58, which is also the back focal plane of lens array 44 then the second beam waist, $W_2$, is located at the lens array, and the third beam waist, $W_3$, is located at the front focal plane of the lens array. Following the Gaussian beam propagation theory, which is known in the art, the spot size diameter of $1/e^2$ at focus is given by:

$$W_3 = \frac{4\lambda f}{\pi W_1} \quad (9)$$

where f, as shown in FIG. 5, is the focal length of the lens array. The beam diameter at the lens aperture is given by:

$$W_2 = W_1 \sqrt{1 + \left(\frac{4\lambda f}{\pi W_1^2}\right)^2} \quad (10)$$

The lens diameter, D, as shown in FIG. 5, is given by:

$$D = kW_3 \quad (11)$$

where k is the truncation ratio defined by the lens clear aperture diameter to the $1/e^2$ beam diameter at the lens. The lens clear aperture, and therefore the minimum gap between the lenses, generally needs to be >1.4× of the beam diameter to avoid severe ringing at the focal plane. The beam diameter at the DOE is given by:

$$W_0 = W_1 \sqrt{1 + \left(\frac{4\lambda L}{\pi W_1^2}\right)^2} \quad (12)$$

where L, as shown in FIG. 5, is the distance from the DOE to the compensating DOE. The angular separation (e.g., $\theta_1$ shown in FIG. 5) between diffracted beams generated by the DOE is given by:

$$\theta_1 \approx \frac{D}{L} \quad (13)$$

when L is much greater than D. The grating pitch of the DOE is then given by:

$$P_1 = \frac{\lambda}{\sin\theta_1} \quad (14)$$

The minimum feature size required to generate the multiple beam is less than:

$$P_m = \frac{P_1}{m} \quad (15)$$

So the distance between the DOE and the compensating DOE, L, needs to be selected such that the minimum feature size of the DOE does not exceed the limits of DOE manufacturing capability. Based on the above equations, an example of a configuration is listed in Table 2.

TABLE 2

| | |
|---|---|
| Wavelength (um) | 0.266 |
| Spot diameter (um) | 6 |
| Spot separation (um) | 1000 |
| Lens array focal length (mm) | 9 |
| Beam diameter at lens array (mm) | 0.51 |
| Truncation ratio | 1.97 |
| Lens diameter (mm) | 1.00 |
| Lens numerical aperture | 0.056 |
| Beam diameter at grating array (mm) | 0.51 |
| Distance between DOE and grating array (mm) | 500 |
| Beam diameter at DOE (mm) | 0.61 |
| Angular separation (rad) | 0.002 |
| DOE pitch (um) | 133 |
| Number of spots | 17 |
| Minimum pitch (um) | 16.63 |
| Relay lens focal length (mm) | 240 |
| Objective lens focal length (mm) | 60 |
| Spot size on sample surface (um) | 1.5 |
| Spot separation on sample surface (um) | 250 |
| Total length of optics (mm) | 1118 |

The numbers listed in Table 2 show that the configuration is practical, but other variations are possible. The array of spots on the wafer may be a one-dimensional array of spots. The spots preferably do not overlap with each other on the wafer. In addition, a size of each of the spots on the wafer may be approximately equal. Furthermore, all of the spots imaged on the wafer may be diffraction-limited spots.

Figure 6:
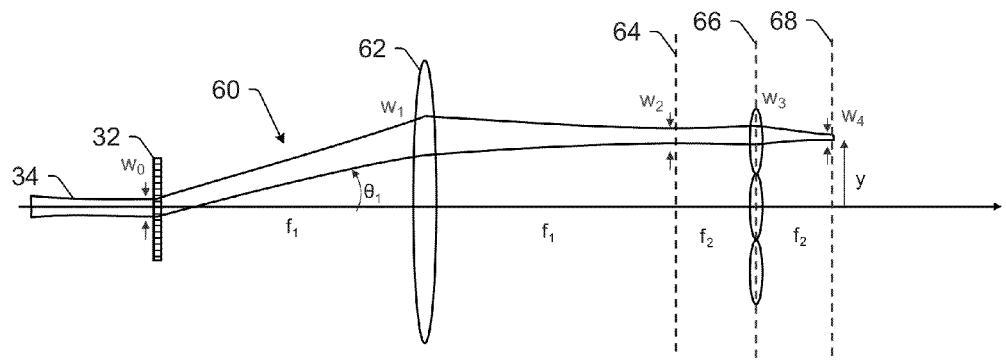

Instead of the compensating DOE described above, the illumination subsystem may include a refractive lens array positioned in the path of the multiple light beams. For example, based on Gaussian beam propagation theory (see S. Self, "Focusing of spherical Gaussian beams", App. Opt., Vol. 22, No, 5, P658, 1983), when the input beam waist is located at the back focal plane of a positive lens, the output beam waist is located at the front focal plane. In this manner, the compensating DOE may be replaced with a lens, with proper arrangement of beam waist locations, to achieve relatively large tolerance to laser bandwidth. The concept is shown in FIG. 6. For example, as shown in FIG. 6, DOE 32 is configured to separate illumination light beam 34 into multiple light beams 60, only one of which is shown in FIG. 6. Refractive lens 62 may be configured to focus the multiple light beams to back focal plane 64 of refractive lens array 66. Refractive lens array 66 may be configured to focus the multiple light beams to front focal plane 68.

The spot diameters (i.e., the diameters of the multiple light beams) at the back focal plane of the refractive lens array are:

$$W_2 = \frac{4\lambda f_1}{\pi W_0} \quad (16)$$

where $\lambda$ is the wavelength of the illumination light beam, $f_1$, as shown in FIG. 6, is the focal length of the refractive lens positioned between the DOE and the refractive lens array, and $W_0$, as shown in FIG. 6, is the diameter of the illumination light beam at the DOE. Diameters of the multiple light beams at the focal plane of the refractive lens array are:

$$W_4 = \frac{4\lambda f_2}{\pi W_2} \quad (17)$$

$$= \frac{f_2}{f_1} W_0$$

where $f_2$, as shown in FIG. 6, is the focal length of the refractive lens array. Diameters of the multiple light beams at the refractive lens array are:

$$W_3 = W_4 \sqrt{1 + \left(\frac{4\lambda f_2}{\pi W_4^2}\right)^2} \quad (18)$$

$$= W_0 \sqrt{\left(\frac{f_2}{f_1}\right)^2 + \left(\frac{4\lambda f_1}{\pi W_0^2}\right)^2}$$

The refractive lens array is configured to relay the laser beam waist at the DOE onto a wafer surface and to separately and simultaneously focus each of the multiple light beams to a wafer for inspection. In one embodiment, the lenses in the refractive lens array have clear apertures (not shown) that are greater than the diameters of the multiple light beams at the refractive lens array. For example, it may be important that the lens clear aperture is greater than the beam diameter to have enough margins to achieve good spot quality and minimize cross talk between the spots. An example of one such configuration is listed in Table 3.

TABLE 3

| | |
|---|---|
| Wavelength (um) | 0.266 |
| Spot diameter W4 (um) | 6 |
| Spot separation (um) | 1000 |
| Lens array focal length (mm) | 4.00 |
| Lens L1 focal length (mm) | 500 |
| Beam diameter at DOE (um) | 750 |
| Beam diameter at lens array (um) | 225.87 |
| Beam truncation ratio at lens array | 4.43 |
| Angular separation (rad) | 0.002 |
| DOE pitch (um) | 133 |
| Relay lens focal length (mm) | 240 |
| Objective lens focal length (mm) | 60 |
| Spot size on sample surface (um) | 1.50 |
| Spot separation on sample surface (um) | 250 |
| Total length of optics (mm) | 1608 |

Figure 7:
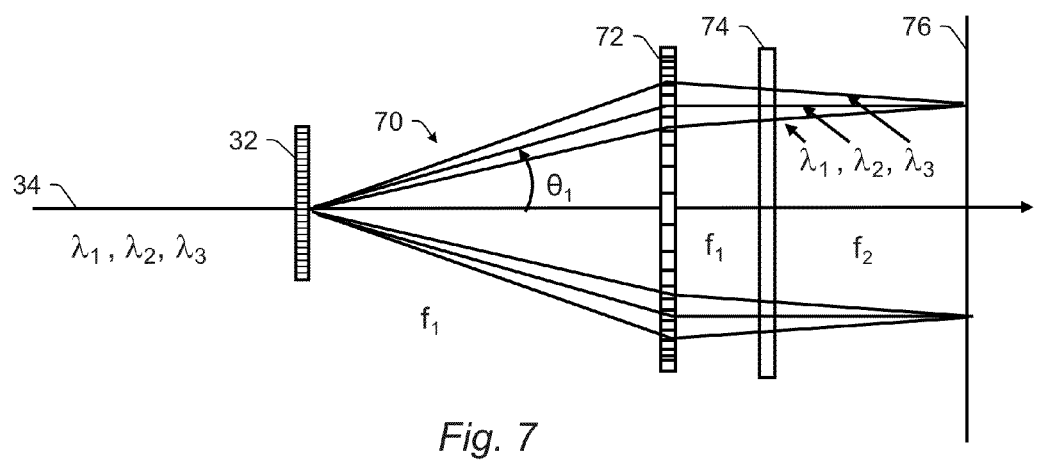

In one embodiment, the compensating DOE is a one-dimensional (1D) chirped grating, and the one or more refractive optical elements include a cylindrical lens. One such embodiment is shown in FIG. 7. For example, DOE 32 may separate illumination light beam 34 having wavelengths $\lambda_1$, $\lambda_2$, and $\lambda_3$ into multiple light beams 70, which are directed to compensating DOE 72. In this embodiment, compensating DOE 72 is a 1D chirped grating. The 1D chirped grating is used to focus the multiple beams in one dimension that is parallel to the plane of drawing and, at the same time, provide compensation of DOE dispersion. Light exiting the 1D chirped grating may be directed to cylindrical lens 74, which separately and simultaneously focuses each of the multiple light beams to focal plane 76, which may be the wafer plane. As shown in FIG. 7, the 1D chirped grating may have focal length $f_1$, white the cylindrical lens may have a focal length of $f_2$. The cylindrical lens provides focusing power in the perpendicular direction. The focus of the 1D chirped grating and the cylindrical lens coincide at the same focal plane 76.

Another embodiment of the illumination subsystem includes a set of beam splitters configured to separate an illumination light beam into multiple light beams and to separately and simultaneously direct the multiple light beams to multiple spatially separated spots on a focal plane. The illumination light beam may include any of the illumination light beams described herein. For example, in one embodiment, the illumination light beam is provided by a pulsed laser and has a central wavelength of 266 nm. In another embodiment, the bandwidth of the illumination light beam is equal to or greater than 10 pm. In addition, in one embodiment, the multiple light beams have the same bandwidth. In other words, the beam splitters included in the set are not used to separate the illumination light beam based on wavelength.

Figure 8:
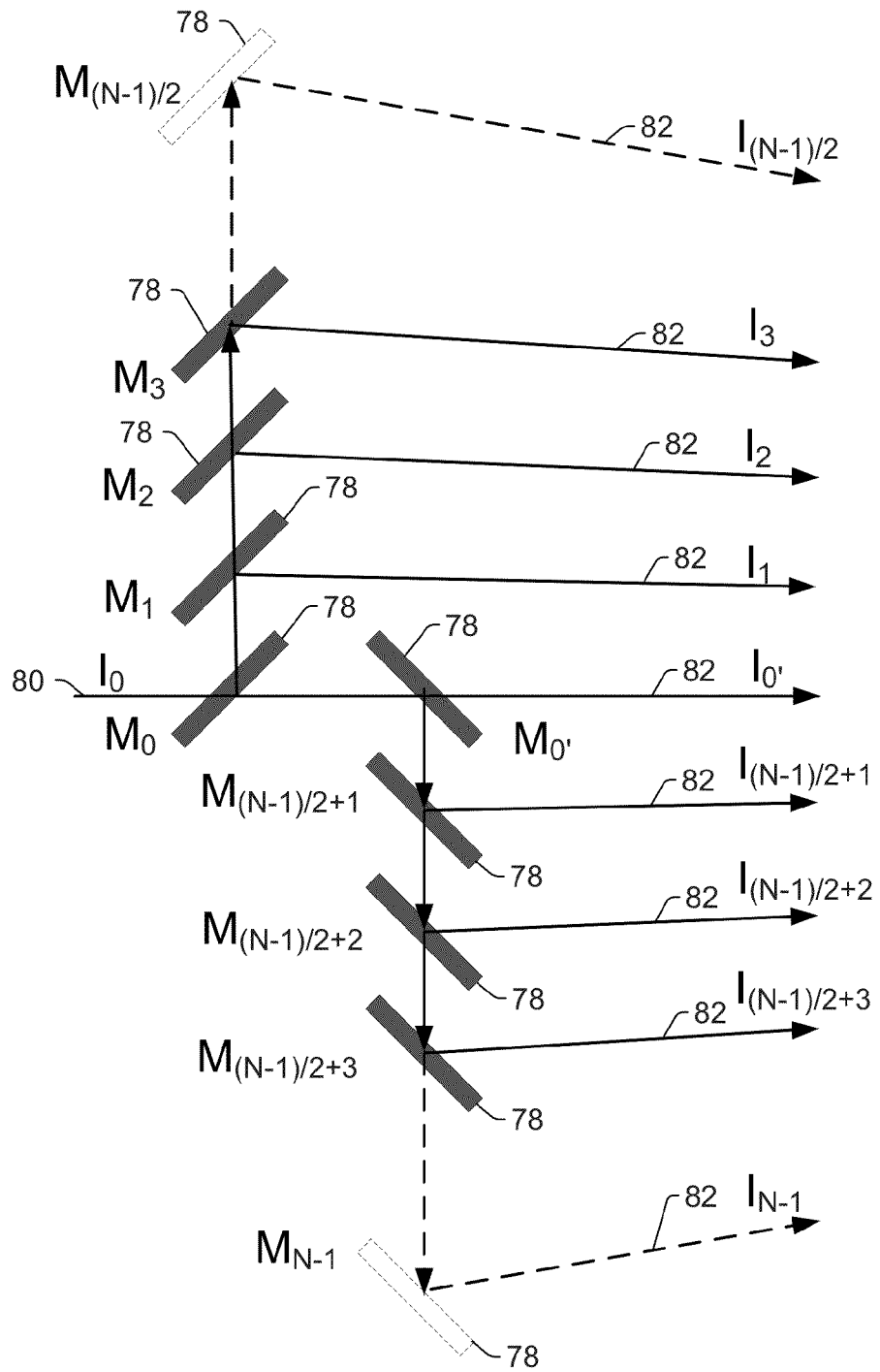
FIGS. 8-11 are schematic diagrams illustrating side views of portions of embodiments of illumination subsystems.

One such embodiment is shown in FIG. 8. For example, as shown in FIG. 8, a set of beam splitters 78 is configured to separate illumination light beam 80 into multiple light beams 82. The illumination light beam may have an input beam diameter of $D_0$. In one embodiment, the number of the multiple light beams is N, and the number of the beam splitters included in the set is N+1. For example, a set of N+1 Beam Splitters/Mirrors (BSMs) may be used to generate a set of N beams. This mirror based system has no dispersive power and can, in principle, be used for a laser source of any bandwidth. The only limiting factor will be the coating technology.

Figure 9:
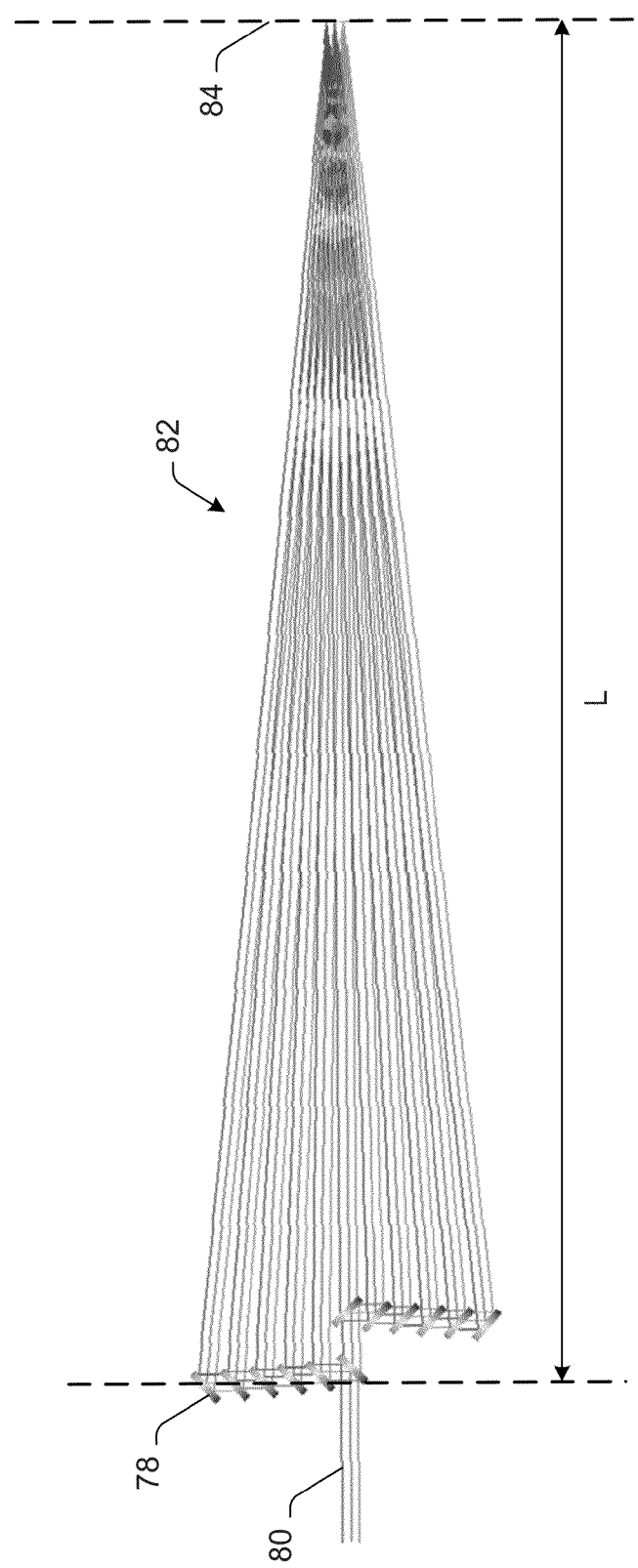

In one embodiment, the set of beam splitters includes first and second beam splitters (e.g., $M_0$ and $M_{0'}$, respectively, shown in FIG. 8) arranged in series, a first subset of the beam splitters (e.g., $M_1$, $M_2$, $M_3$, ... $M_{(N-1)/2}$ shown in FIG. 8) arranged in series with the first beam splitter (e.g., $M_0$ shown in FIG. 8), and a second subset of the beam splitters (e.g., $M_{(N-1)/2+1}$, $M_{(N-1)/2+2}$, $M_{(N-1)/2+3}$, ... $M_{N-1}$ shown in FIG. 8) arranged in series with the second beam splitter (e.g., $M_{0'}$ shown in FIG. 8), and the illumination light beam is directed to the first beam splitter. In this manner, an input beam of diameter $D_0$ is split into 2 beams via the action of the first beam splitter $M_0$. The beam travelling upwards is further spill/transmitted by the series of BSMs, $M_1$, $M_2$, $M_3$, ..., $M_{(N-1)/2}$. In one embodiment, inclination angles of the beam splitters are set such that each of the multiple light beams converges toward an optics axis of the illumination subsystem. For example, the inclination angle of each BSM may be set such that each of the reflected beams converges towards the optic axis at angles, $\alpha$, $2\alpha$, $3\alpha$, ..., $(N-1)/2\alpha$. The beam transmitted through BSM $M_0$ is further split/transmitted by the action of a second BSM, $M_{0'}$. The beam transmitted by $M_{0'}$ emerges from the it) illumination subsystem to form the axial, undeviated beam, while the vertical lower reflected beams follow the same pattern of transmission/reflection via the action of the set of BSMs labeled $M_{(N-1)/2+1}$, $M_{(N-1)/2+2}$, ..., $M_{(N-1)}$ in FIG. 8. The various reflected beams will converge to a single plane (e.g., exit pupil 84 of the device as shown in FIG. 9).

The illumination subsystem also includes one or more refractive optical elements (not shown in FIG. 8) configured to separately and simultaneously focus each of the multiple light beams from the focal plane to a wafer for inspection. For example, the one or more refractive optical elements, which may include any of those shown and described 213 further herein, may include an objective or an objective in combination with relay optics. Such refractive optical element(s) may be further configured as described further herein. In this manner, the exit pupil of the portion of the illumination subsystem shown in FIG. 8 could represent the entrance pupil of an objective lens or could be relayed to the entrance pupil of the objective via the action of a relay lens with a pre-determined magnification/de-magnification.

The vertical distance between the BSMs, H, and inclination angle, $\alpha$, is determined by the input beam diameter, $D_0$, and the need for the reflected beams to clear the edges of the BSMs. These two parameters in turn will determine the distance, L, from the BSMs to the exit pupil:

$$L = \frac{H}{\tan\alpha} \quad (19)$$

For example, if the entrance pupil diameter is 2.0 mm and the exit pupil diameter is 2.0 mm, then the distance from the BSMs to the exit pupil may be approximately 357 mm. In one embodiment, the power of the illumination light beam is substantially uniformly distributed across the multiple tight beams. For example, for a substantially uniform distribution of the input laser power amongst the various output beams generated by this illumination subsystem, the reflectivities of the individual BSMs can be calculated using the set of formulas and in the order shown below. The derivation assumes zero loss due to absorption and other factors: Power per generated beam:

$$P_n = P_0 \frac{T^{(N-1)}}{N}, n = 1, 2, 3, \ldots, N \quad (20)$$

where $P_0$=input power, and T=transmission through the non-reflective surface of a BSM.
Reflectivity of $M_0$:

$$R_0 = \frac{T[N - T^{(N-3)}]}{N(1+T)}, \quad (21)$$

Reflectivity of $M_{0'}$:

$$R_{0'} = \frac{R_0}{T(1-R_0)}, \quad (22)$$

Power incident on $M_1$:

$$P_{i1} = P_0 R_0, \quad (23)$$

Reflectivity of $M_1$:

$$R_1 = \frac{P_1}{P_{i1}}, \quad (24)$$

Power incident on subsequent mirrors, $M_2, M_3, \ldots, M_{N-1}$:

$$P_{in} = P_{i(n-1)} T[1 - R_{(n-1)}], n=2,3,\ldots,N-1 \quad (25)$$

Finally, the reflectivity of BSMs 2 through N−1 is given by:

$$R_n = P_n/P_{in}, n=2,3,\ldots,N-1 \quad (26)$$

Through repeated application of equations 25 and 26, the reflectivities of all of the mirrors can be calculated.

An example of a configuration for generation of 11 beams is shown in FIG. 9 and Table 4.

TABLE 4

| | |
|---|---|
| Number of generated beams | 11 |
| Input power | 1.0 Watts |
| Transmission of A-R coatings | 98% |
| Power per generated beam | 0.074 Watts |
| Total transmitted power | 0.82 Watts |

TABLE 4-continued

| Mirror Reflectivities: | |
|---|---|
| Mirror ID | % Reflectivity |
| M1 & M6 | 16.27 |
| M2 & M7 | 19.82 |
| M3 & M8 | 25.23 |
| M4 & M9 | 34.43 |
| M5 & M10 | 53.57 |

Figure 10:
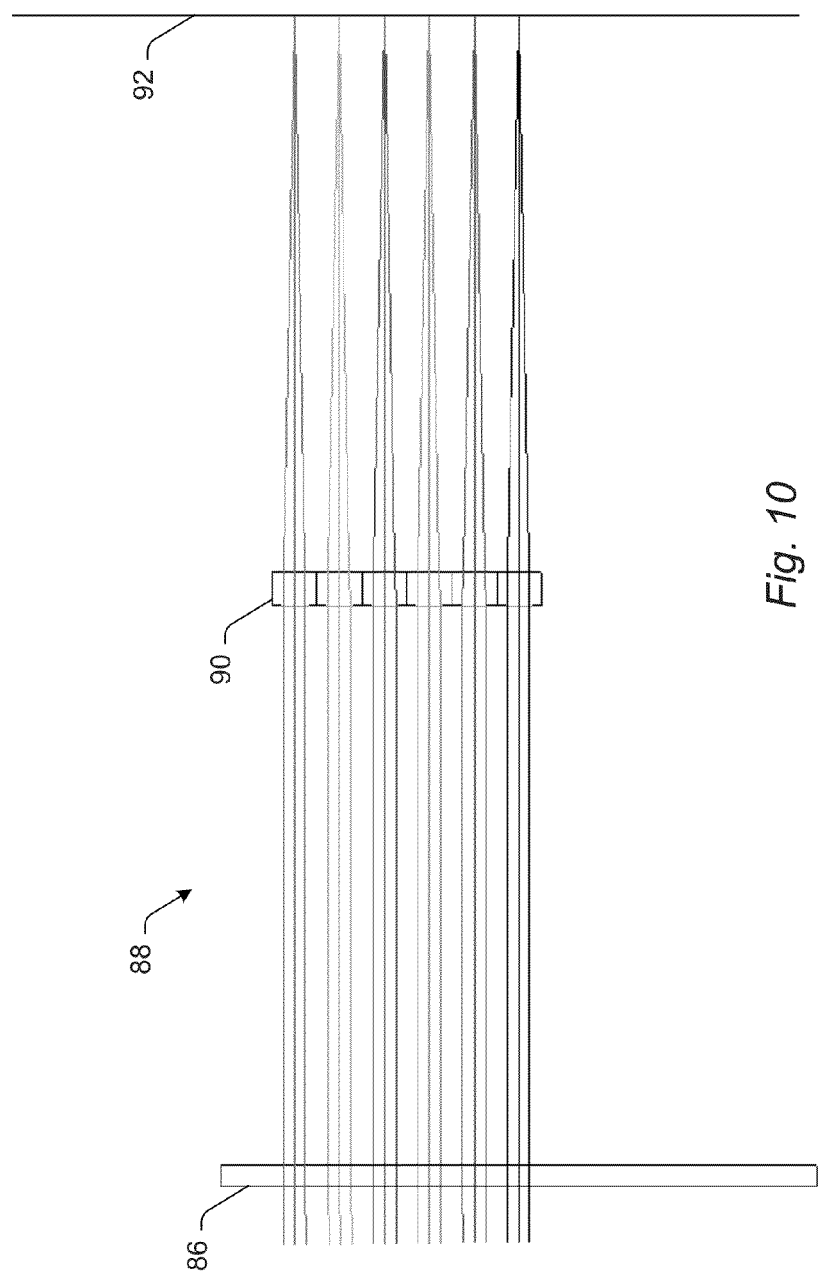
Figure 11:
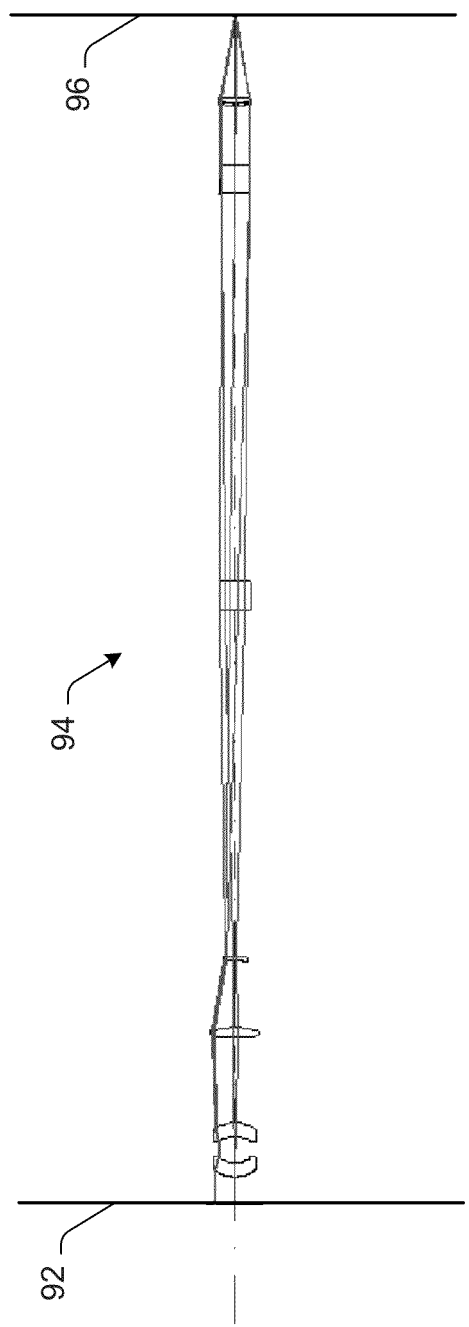
Figure 12:
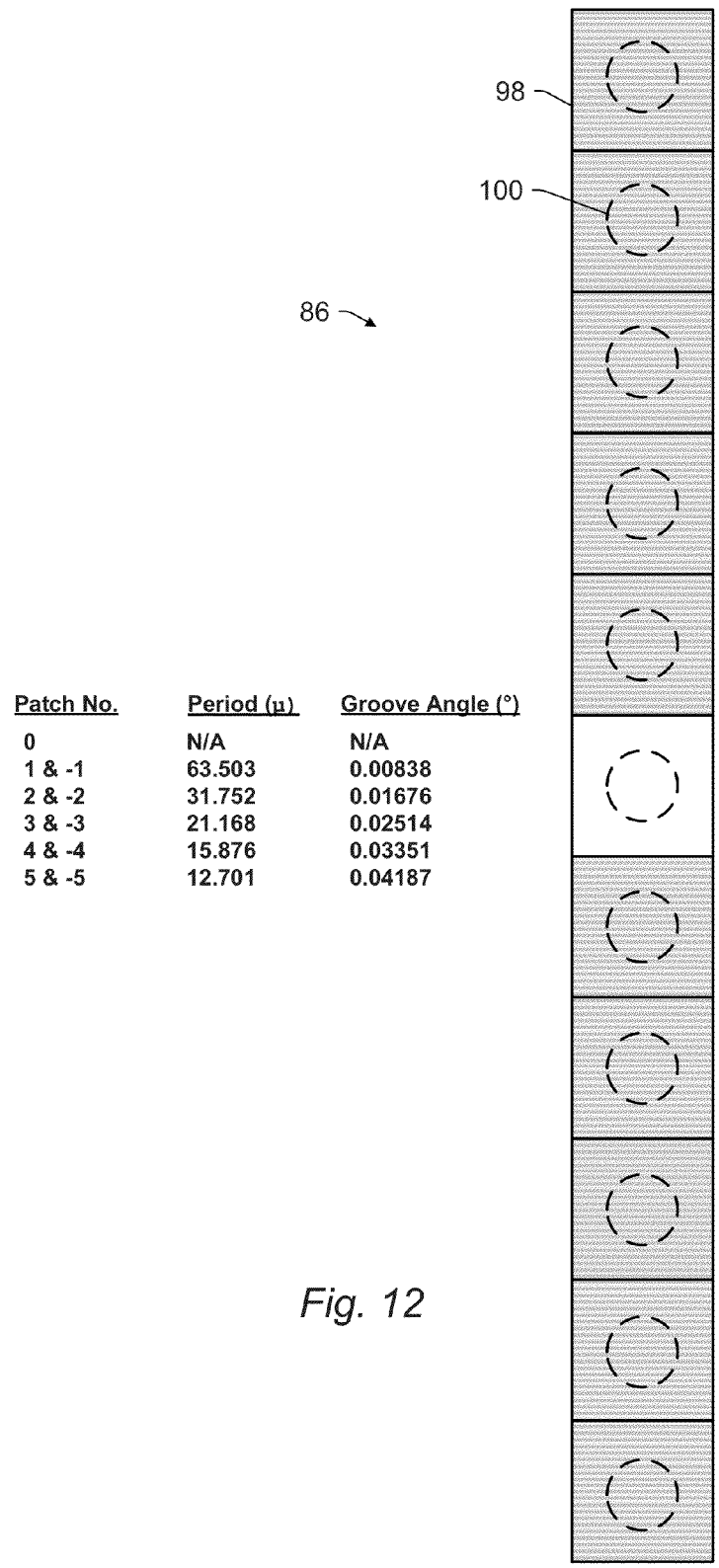
FIG. 12 is a schematic diagram illustrating a cross-sectional view of one embodiment of a compensating DOE that may be used in embodiments described herein.

An example of an implementation of one embodiment is shown in FIGS. 10-12 and Table 5 for the case of 11 beams. In particular, FIG. 10 illustrates an embodiment of a blazed grating/lens array arrangement. As shown in FIG. 10, the illumination subsystem includes compensating DOE 86, which in this embodiment is a blazed grating. Multiple light beams 88 exiting the compensating DOE are directed to one or more refractive optical elements, which in this case include lens array 90. Lens array 90 separately and simultaneously focuses each of the multiple light beams to focal plane 92. The distance between the compensating DOE and the DOE (not shown in FIG. 10) may be about 955 mm. The focal length of lens array 90 may be about 50 mm.

This embodiment of the illumination subsystem may also include relay optics configured as described herein to relay the multiple light beams from focal plane 92 to a wafer plane (not shown in FIG. 10). For example, FIG. 11 shows one embodiment of a final relay optics layout. As shown in FIG. 11, relay optics 94 may include a number of different refractive optical elements configured to relay the multiple light beams from lens array focal plane 92 to image/wafer plane 96. The distance between the lens array focal plane and the image/wafer plane may be approximately 1238 mm.

FIG. 12 shows one embodiment of characteristics of the blazed grating shown in FIG. 10. For example, as shown in FIG. 12, blazed grating 86 may include patches 98. The blazed grating may include 11 patches, one for each of the 11 multiple light beams. Each of the patches may have dimensions of 4 mm×4 mm. Each of the patches may have active area 100. Each of the active areas may have a diameter of 2 mm. Each of the patches may have the period and groove angles included in the table shown in FIG. 12.

TABLE 5

| | |
|---|---|
| Entrance pupil diameter | 2 mm |
| Input beam diameter at waist | 1 mm |
| Wavelength | 266 nm ± 75 pm |
| Angular separation between diffracted orders | 0.24° |
| Lens array effective focal length | ≃52 mm |
| Lens array diameter | 5 mm |
| Spot separation at lens array focal plane | 4.0 mm |
| Lens array focused spot diameter at waist | 35 um |
| Relay optics input field diameter | 40 mm |
| Relay optics output field diameter | 2.5 mm |
| Focused spot diameter at waist | 2 um |
| Focused spot separation | 250 um |

It is noted that the figures are provided herein to generally illustrate configurations for the illumination subsystem embodiments described herein. Obviously, the configurations described herein may be altered to optimize the performance of the illumination subsystem as is normally performed when designing an illumination subsystem for a commercial wafer inspection system.

Further modifications and alternative embodiments of various aspects of the invention may be apparent to those skilled in the art in view of this description. For example, illumination subsystems for multi-spot wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An illumination subsystem configured to provide illumination for wafer inspection, comprising:
    a set of beam splitters configured to separate an illumination light beam into multiple light beams and to separately and simultaneously direct the multiple light beams to multiple spatially separated spots on a focal plane, wherein inclination angles of the beam splitters are set such that each of the multiple light beams converges toward an optics axis of the illumination subsystem as it exits its respective beam splitter; and
    one or more refractive optical elements configured to separately and simultaneously focus each of the multiple light beams from the focal plane to a wafer for inspection.

2. The illumination subsystem of claim 1, wherein the illumination beam is provided by a pulsed laser and has a central wavelength of 266 nm.

3. The illumination subsystem of claim 1, wherein the bandwidth of the illumination light beam is equal to or greater than 10 pm.

4. The illumination subsystem of claim 1, wherein the multiple light beams have the same bandwidth.

5. The illumination subsystem of claim 1, wherein the number of the multiple light beams is N, and wherein the number of the beam splitters included in the set is N+1.

6. The illumination subsystem of claim 1, wherein the set of beam splitters comprises first and second beam splitters arranged in series, a first subset of the beam splitters arranged in series with the first beam splitter, and a second subset of the beam splitters arranged in series with the second beam splitter, and wherein the illumination light beam is directed to the first beam splitter.

7. The illumination subsystem of claim 1, wherein the power of the illumination light beam is substantially uniformly distributed across the multiple light beams.

* * * * *